United States Patent [19]

Hedges

[11] Patent Number: 5,554,128
[45] Date of Patent: Sep. 10, 1996

[54] SYRINGE AND VIAL CONNECTOR

[75] Inventor: Harry S. Hedges, Kalamazoo, Mich.

[73] Assignee: Joseph K. Andonian, Portage, Mich.

[21] Appl. No.: 370,020

[22] Filed: Jan. 9, 1995

Related U.S. Application Data

[63] Continuation-in-part of Ser. No. 208,142, Mar. 9, 1994, Pat. No. 5,520,659.

[51] Int. Cl.$^6$ ................................................. A61M 5/32
[52] U.S. Cl. ...................... 604/192; 604/414; 604/905; 141/27
[58] Field of Search ..................... 604/192, 240, 604/242, 243, 407, 414, 416, 905, 411, 195, 403, 197, 110; 141/18, 21, 25–27, 108, 326, 327, 329, 330, 97, 383, 386, 368, 369, 370, 372, 384; 128/764, 770, 919; 215/26–28, 325, DIG. 5

[56] References Cited

U.S. PATENT DOCUMENTS

| | | | |
|---|---|---|---|
| 4,475,915 | 10/1984 | Sloane | 604/414 |
| 5,067,950 | 11/1991 | Broadnax, Jr. | 604/317 |
| 5,088,996 | 2/1992 | Kopfer et al. | 604/415 |
| 5,158,558 | 10/1992 | Melker et al. | 604/411 |
| 5,247,972 | 9/1993 | Tetreault | 141/27 |

*Primary Examiner*—Randall L. Green
*Assistant Examiner*—V. Alexander
*Attorney, Agent, or Firm*—Joseph K. Andonian

[57] ABSTRACT

A tubular sleeve suitable for connecting a disposable hypodermic syringe to a medicinal vial without exposing the tip of the needle until the syringe is filled and ready for injection. A process of inserting the syringe with a cap covering the needle into the first end of the sleeve, removing the needle cap, inserting the vial cap into the second end of the sleeve which allows the needle to penetrate the stopper in the vial and withdrawing medicament into the syringe.

5 Claims, 2 Drawing Sheets

5,554,128

SYRINGE AND VIAL CONNECTOR

CROSS-REFERENCE TO PREVIOUS APPLICATIONS

This application is a continuation-in-part of U.S. patent application Ser. No. 08/208,142 filed Mar. 9, 1994, now U.S. Pat. No. 5,520,659.

TECHNICAL FIELD

This invention relates to a product and process for safely and conveniently connecting a disposable syringe to a medicinal vial. The syringe can be inserted into one end of the device with a protective cap covering the syringe needle. The cap can then be safely removed from the needle without exposing the point of the needle to the user. Finally the vial can be attached to the other end of the device and the syringe can be filled in the usual manner. The principal advantages of the device are safety, economy and ease of use.

BACKGROUND PRIOR ART

The prior art contains many examples of devices intended to facilitate the task of mating a syringe to a vial for the purpose of extracting medicament from the vial. U.S. Pat. No. 5,240,047 issued to the present inventor is one example of such a device. U.S. Pat. No. 5,247,972 is another example. Both patents list several patents disclosing related devices cited during the prosecution of the patents. However, no prior art device possesses the same advantages as the present invention. For example, in order to use the devices disclosed in U.S. Pat. Nos. 5,240,047 and 5,247,972 the cap on the needle must be removed before the syringe can be inserted into either device. Handling the syringe with an exposed needle increases the risk of injury to the user and also damage to the needle itself. The device disclosed in U.S. Pat. No. 5,247,972 is also more expensive to produce and more difficult to use than the present invention.

The present invention is a continuation of the effort to provide devices that are safer and easier to use especially for untrained individuals who inject medications to themselves or family members. Greater economy and simplicity are also desirable goals especially in the face of rising health care costs. The present invention differs from the invention covered in my above-identified parent application primarily in it applicability to syringes that have a large diameter barrel. The present device will fit over the needle cap on such a syringe and therefore can be used with such commercially available syringes without changing the syringes. The device of my parent application acts as a substitute for the needle cap for syringes where the barrel of the syringe has a diameter almost equal to that of the needle cap. Both the devices of my parent application and the present application are superior to the device claimed in my U.S. Pat. No. 5,240,047 in limiting the user's exposure to the needle until the syringe is filled and ready for injection.

OBJECTS OF THE INVENTION

The principal object of the present invention is to provide a device for connecting a disposable syringe to a medicinal vial with greater safety to and ease of accomplishment by the user.

Another object of the present invention is to provide such a device that is more economical than prior art devices.

Other objects will be apparent from the following description.

SUMMARY OF THE INVENTION

The present invention accomplishes the foregoing objectives by providing a device that can be connected at one end to a hypodermic syringe with a cap covering the syringe needle and to a medicinal vial at the other end after the cap on the needle is removed. When connected, the syringe vial, and connecting device are coaxially aligned.

Syringes are normally supplied commercially with a cap covering the needle to help preserve sterility and protect the needle. The present device comprises a tubular sleeve having a first end and a second end. The first end possesses an internal bore that is adapted to receive and hold the lower portion of the syringe barrel firmly but removably with the capped needle also loosely housed within the sleeve. A stop is provided within the bore at the first end to limit the penetration of the syringe barrel to a point where the syringe is held firmly enough to facilitate extraction of the contents of the vial when the latter is attached. Generally, penetration from about one-quarter to about one-half of the length of the barrel is sufficient. A second stop is provided within the bore at the second end to limit the penetration of the capped top portion of a medicinal vial. Fully enclosing the cap of the vial within the second end of the sleeve is generally sufficient to hold the vial firmly but removably until the syringe is filled. The second end of the sleeve is also adapted to permit the user of the device to grasp and remove the needle cap before the vial is attached. The length of the sleeve and the distance between the stops is adjusted to enable the needle to penetrate the stopper on the end of the vial so that the contents of the vial can be extracted. The second end of the sleeve beyond the stop is also adapted to shield the needle tip so that the user will have no opportunity to contact the point of the needle during removal of the needle cap and subsequent use of the device to facilitate extraction of the contents of the vial. The needle will thus be fully exposed only after the syringe is filled with medicament and disconnected from the sleeve. The needle will also enter the vial at an angle that is perpendicular to the top surface of the vial to prevent bending or blunting the tip of the needle.

Figure 1A:
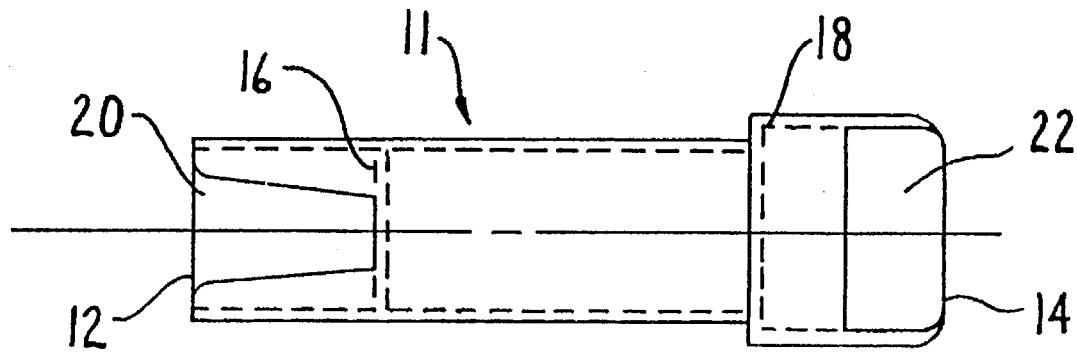
FIG. 1A provides a plan view of the tubular sleeve.

The figures are not drawn to exact scale.

Reference numerals used in the drawings

1 Hypodermic syringe
2 Syringe plunger
4 Syringe barrel
6 Syringe needle cap
8 Syringe needle
10 Indicia on barrel of syringe
11 Tubular sleeve
12 First end of tubular sleeve
14 Second end of tubular sleeve
16 Shoulder (stop) in first end of tubular sleeve
18 Shoulder (stop) in second end of tubular sleeve 20 Slotted opening in first end of tubular sleeve
21 Medicinal vial
22 Opening in second end of tubular sleeve
26 Vial cap
27 Bull's eye on top of vial
28 Vial stopper
30 Tip of needle
32 Boss at needle end of syringe barrel

DETAILED DESCRIPTION

Figure 2:
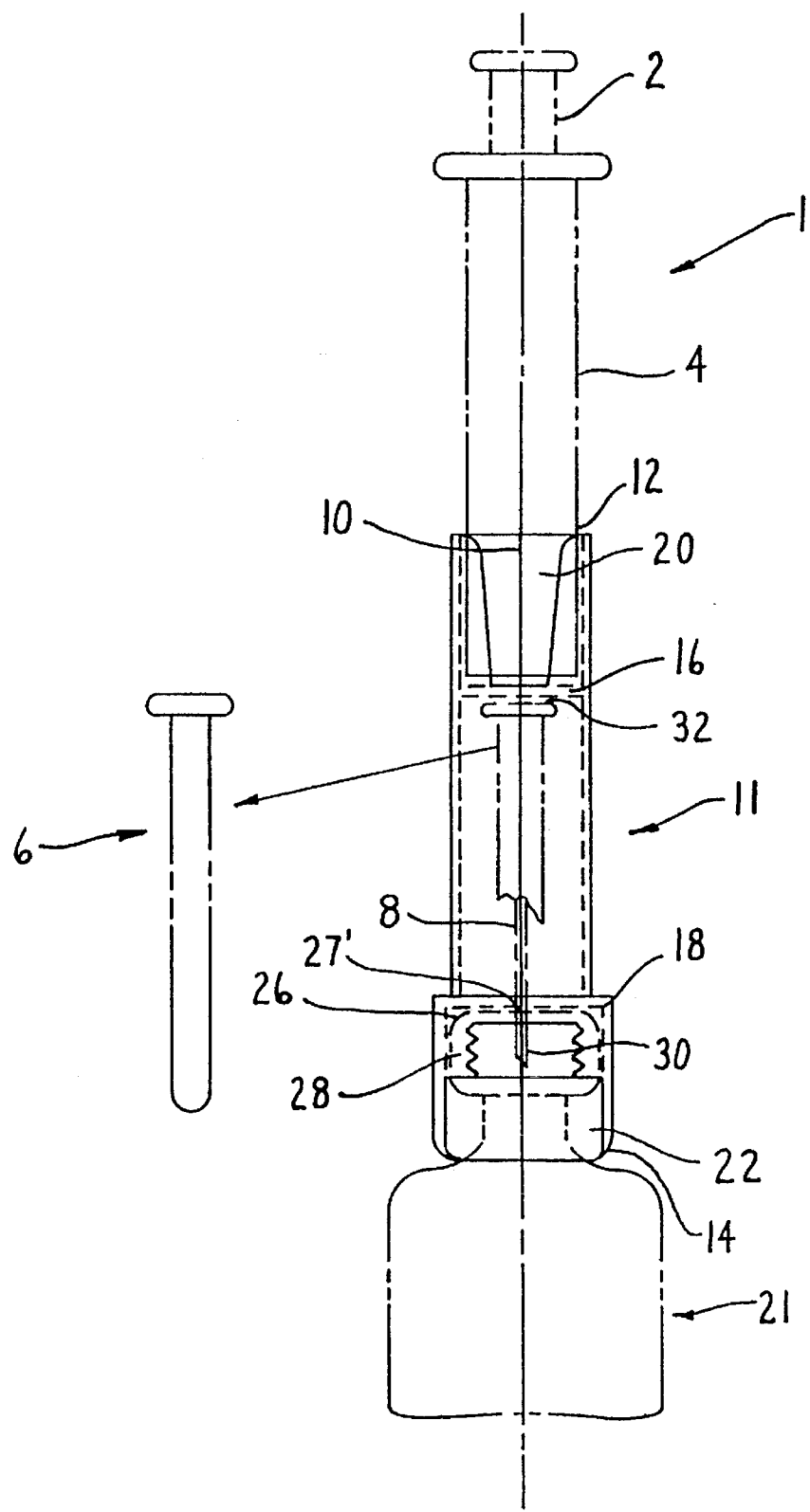
FIG. 2 depicts a syringe connected to a vial by the tubular sleeve of FIGS. 1A, 1B and 1C.

The syringe depicted by phantom lines in FIG. 2 is a typical commercially available disposable syringe used in medical practice to inject medicaments. In normal usage the needle cap 6 is removed, the needle 8 is inserted into the opening or bulls eye 27 found on top of a vial 21 depicted by phantom lines in FIG. 2, the desired quantity of medicament is extracted from the vial 21, and the filled syringe 1 is used to inject the medicament into a patient. While practiced individuals such as nurses have relatively little difficulty using syringes in the manner indicated under ordinary circumstances, users who are less experienced, less dexterous, visually impaired or simply distracted or rushed can accidentally bend or blunt the needle or inappropriately jab themselves or their patients with the needle. Even experienced nurses can blunt the point of a needle when filling a syringe, especially if they miss the bulls eye 27 or attempt to penetrate a vial stopper at less than a full 90 degree angle to the top surface of the vial. At least in part for that reason, nurses often use one needle to extract the contents of a vial and a different unused needle for injecting the patient. Poor vision, especially among diabetics, is most likely to lead to unsafe practices. Infective organisms can also be transmitted between the user and the patient if both are accidentally jabbed with the same needle. Bending or blunting the point of a needle can lead to increased pain or tissue damage upon injection. The present invention is designed to minimize such difficulties.

Although the syringe 1 is generally empty and the fluid medicament is extracted entirely from the vial 21, occasionally the dry medicament and the fluid diluent are stored separately prior to use. The syringe barrel 4 can house one of the components and the vial 21 the other. Mixture occurs just prior to use. Greater stability of the medicament is the primary objective when this is done. When the diluent is stored in the syringe barrel 4, the diluent is injected into the vial 21 and mixed with the dry powdered medicament prior to withdrawal of the reconstituted preparation into the syringe 1 prior to injection into the patient. When the dry medicament is stored in the syringe barrel 4, the diluent is stored in the vial 21 and mixing is carried out in the syringe barrel 4 after the diluent is extracted from the vial 21.

Figure 1B:
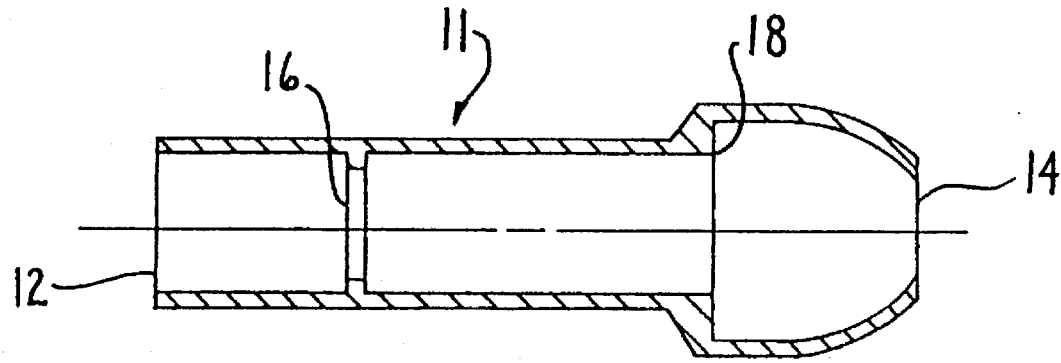
FIG. 1B depicts a cross-sectional view of the tubular sleeve taken along the line II—II of FIG. 1C.
Figure 1C:
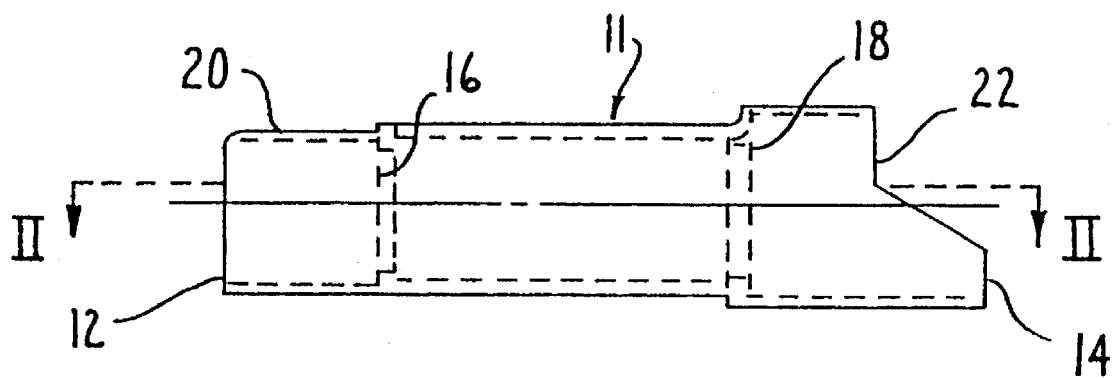
FIG. 1C provides another view of the tubular sleeve rotated 90 degrees from the perspective shown in FIG. 1A.

To use the device of the present invention, the empty syringe 1 can be inserted into the first end 12 of sleeve 11 depicted in FIGS. 1A, 1B and 1C until the barrel 4 butts up against shoulder 16. The sleeve 11 is sized so that the closed end of needle cap 6 will extend into the opening at the second end 14. The closed end of needle cap 6 which extends beyond the point 30 of needle 8 can be grasped between the fingers and removed manually without touching the needle. The second end 14 is sized to extend completely around and just beyond the point 30 of the needle 8. The cap 26 of vial 21 can be inserted into the second end 14 of sleeve 11 until the top of the cap 26 butts up against shoulder 18. The top of the vial 21 in a standard commercial embodiment consists of a stopper 28 in the neck of the vial 21 enclosed by a metal cap 26 which is crimped over the top of the vial 21. The metal cap 26 has a small round opening or bulls eye 27 in the top center of the cap 26 which provides an unobstructed passage for the needle 8 into and through the stopper 28. The stopper 28 is thinner at the bulls eye 27 to allow easier entry of the needle 8 into the vial 21. The medicament can then be extracted from vial 21 in the desired quantity, the syringe 1 can be separated from the sleeve 11 and is ready for injection. FIG. 2 depicts the syringe 1, vial 21 and sleeve 11 in coaxial alignment and ready to fill the syringe 1.

The distance between the stops 16 and 18 should be adjusted to fit the pertinent dimensions of the syringe 1 and the vial 21. The distance between the bottom of the syringe barrel 4 and the tip 30 of needle 8 should be greater than the distance between the face of stop 16 where it contacts the bottom of syringe barrel 4 after insertion into sleeve 11 and the inside surface of stopper 28 at the bull's eye 27 when vial 21 is fitted against stop 18 in sleeve 11. If complete extraction of the contents of vial 21 is intended, the pertinent dimensions of sleeve 11 should be adjusted to allow the tip 38 of needle 8 to penetrate just inside the stopper 28 at bull's eye 27. The overall shape of sleeve 11 should preferably be cylindrical. However, the outside configuration is not critical as long as the inside configuration fits the syringe barrel 4 at first end 12, the cap 26 of vial 21 at second end 14 and the intervening bore of sleeve 11 can loosely enclose needle cap 6.

The slotted opening 20 in the first end 12 of the sleeve 11 is provided in a preferred embodiment of the invention to permit an unobstructed view of the indicia 10 on the syringe barrel 4. The proper dosage of medicament can thereby be withdrawn into the syringe 1 for administration. After insertion of syringe barrel 4 into first end 12, the syringe 1 is turned to align the indicia 10 inside the slotted opening 20.

The opening 22 cut out of the second end 14 of the sleeve 11 is provided in a preferred embodiment of the invention to permit unobstructed viewing of the contents of the vial 21. The configuration best pictured in FIG. 1C also helps the user to guide the top of the vial 21 into the second end 14 of sleeve 11. It further provides an unobstructed view of the tip 30 of needle 4 through the slotted opening 29 cut into the side of vial stopper 28.

The preferred material for sleeve 11 is a clear, slightly elastic medical grade plastic similar to that used for disposable syringes. An opaque medical grade plastic would also be suitable especially if the openings 20 and 22 are present in both ends of sleeve 11. The ends of sleeve 11 should expand slightly when the syringe 1 and vial 21 are press-fitted into ends 12 and 14. Since the sleeve 11 will not ordinarily come into contact with the medicament, the needle or the patient, almost any slightly elastic plastic can be used for sleeve 11.

If the medicament to be drawn into the syringe barrel 4 is substantially transparent the indicia 10 placed on the syringe barrel 4 to indicate the volume of space inside the barrel 4 can be placed on the barrel 4 so they may be read through the medicament and the barrel 4 in magnified form. The transparent medicament itself can act as a magnifier. This would be especially useful for users with impaired vision and is preferable to the more costly separate magnifier provided by other products such as the housing described in U.S. Pat. No. 5,247,972. The indicia 10 on the vial and the level of medicament in the barrel 4 can also be highlighted by using a background color such as bright white or highly reflective paint on the inside surface of the sleeve 11 opposite the position where the indicia 10 on the barrel 4 would normally appear. When the indicia 10 are positioned in the slotted opening 20 by turning the barrel 4, the background of contrasting colors seen directly through the slotted opening 20 will highlight the indicia 10.

The foregoing relates essentially to preferred exemplary embodiments of the present invention, it being understood that other embodiments and variants thereof are possible within the scope of the invention as defined by the legal scope of the appended claims.

What is claimed is:

1. A combination comprising a disposable syringe having a tubular barrel and a capped needle on one end of said barrel and a tubular sleeve mounted over the capped needle end of said syringe wherein said tubular sleeve has a first end, a second end and internal bore means adapted to receive in coaxial alignment said capped needle end of said syringe and a medicinal vial, said first end of said tubular sleeve is fitted firmly but removably over the capped needle end of said syringe, said bore means at said second end of said tubular sleeve is adapted to fit firmly but removably over a medicinal vial having needle penetrable top means suitable for receiving said needle for the purpose of extracting medicament from said vial into the barrel of said syringe without exposing the tip of said needle to the user until said syringe is ready for injecting the medicament from said syringe, said bore means is sufficiently large throughout its entire length to accommodate said cap of said needle and extend beyond the tip of said needle, said sleeve possesses first stop means within said bore means for limiting the penetration of the said syringe barrel into said first end of said sleeve and second stop means within said bore means for limiting the penetration of the top of said vial into said second end of said sleeve, means at the second end of said sleeve adapted to permit the manual removal of said needle cap before attaching said vial without exposing the tip of the needle to the user and the length of said sleeve and the distance between said stops in said bore means is adapted to permit the needle on the end of said syringe to penetrate the top of said vial and extract the contents of said vial when said sleeve is connected to said syringe and said vial.

2. The device of claim 1 wherein the first end of said sleeve possesses means for reading indicia placed on the surface of said syringe barrel to measure the volume of fluid withdrawn into the said syringe barrel.

3. The device of claim 2 wherein said for reading indicia means consists of a slotted opening in said first end of said sleeve sufficient in length and breadth to expose the said indicia on said syringe barrel.

4. The device of claim 1 wherein said sleeve consists of a transparent plastic material.

5. A process for connecting a syringe having a barrel and a capped needle on one end of said barrel to a vial having a needle penetrable top suitable for receiving said needle for the purpose of extracting fluid from said vial to fill the syringe with fluid without exposing the syringe needle to the user until the syringe is ready for injection which process comprises inserting said needle capped end of said syringe into the first end of a tubular sleeve wherein the tubular sleeve comprises an internal bore means adapted to receive in coaxial alignment said syringe barrel at the first end and said vial at the second end wherein the said bore means is capable of holding said barrel and said vial firmly but removably, providing stops to limit the entry of said barrel into said first end and said vial into said second end, housing the said needle cap loosely enough to facilitate manual removal, providing sufficient space between said stops to enable the said needle cap to extend far enough beyond said second end to enable the user to grasp the end of said needle cap and remove it without touching the tip of said needle and yet enable the point of said needle to penetrate the stopper on the top of said vial to facilitate extraction of fluid from said vial, inserting said barrel up to said stop into said first end, manually removing said needle cap, inserting said vial up to said stop into said second end, filling said barrel up to the desired quantity for injection with said syringe, and removing said syringe from said sleeve.

* * * * *